United States Patent [19]

Pühler et al.

[11] Patent Number: 4,686,184

[45] Date of Patent: Aug. 11, 1987

[54] GENE TRANSFER VECTOR

[75] Inventors: Alfred Pühler; Reinhard Simon, both of Bielefeld, Fed. Rep. of Germany

[73] Assignee: Lubrizol Genetics, Inc., Boulder, Colo.

[21] Appl. No.: 510,296

[22] Filed: Jul. 1, 1983

[51] Int. Cl.[4] .................. C12N 15/00; C12N 1/20; C12N 1/00; C12R 1/41

[52] U.S. Cl. .................. 435/172.3; 435/253; 435/878; 435/320; 935/27

[58] Field of Search ............... 435/172.3, 253, 317; 935/22, 23, 26, 27, 29, 66, 72

[56] References Cited

PUBLICATIONS

Simon, R. et al., in *Molecular Genetics of the Bacteria--Plant Interaction*, (A. Puhler, ed), pp. 98–106, 1983.

Berg, De., in *DNA, Insertion, Elements, Plasmids, and Episomes*, (eds. Bukhari, Shapiro, Adhya), pp. 205–212, 1977.

*Mobile Genetic Elements* (ed. James A. Shapiro), pp. 226, 233, 234, 262 and 266, 1983.

Klee, H. J. et al., *J Bacteriol*, vol. 150, pp. 327–331, 1982.

Datta, N., et al., (1971), *J. Bact*, 108:1244–1249.

Datta, N. and R. W. Hedges (1972), *J. Gen. Microbiol.*, 70:453–460.

Olsen, R. H. and P. J. Shipley (1973), *J. Bact.* 113:772–780.

Beringer, J. G. (1974), *J. Gen. Microbiol.*, 84:188–198.

Starlinger, P. (1980), *Plasmid*, 3:241–259.

Calos, H. and J. H. Miller (1980), *Cell*, 20:579–595.

Priefer, U. B., et al., (1980) in *Antibiotic Resistance, Transposition and Other Mechanisms* (S. Mitshuhashi, L. Rosival and V. Krcmery, eds.), Springer–Verlag, Berlin, pp. 91–96.

Simon. R, (1980) in *Antibiotic Resistance, Transposition and Other Mechanisms*, (S. Mitshuhashi, L. Rosival and V. Krcmery, eds.), Springer–Verlag, Berlin, pp. 35–42.

Simon, R. et al., (1983), Analysis of Plasmid Borne Genes in *Rhizobium meliloti* by Tn5 Mutagenesis, Winnipeg Symposia–Proc., 8th N. Amer. Rhizobium Conference, (meeting held in 1981), published Jan. 1983.

*8th North American Rhizobium Conference Abstract Book*, pp. 1–3, 7–15, 20, 22, 25, 28–29, 42–43, 100–103, 105, 128, 130, 132 and 136 (Aug. 3–7, 1981).

*Proceedings, 8th North American Rhizobium Conference*, pp. 90–114 (K. W. Clark & J. H. G. Stephens eds. 1983).

*Primary Examiner*—Alvin E. Tanenholtz
*Assistant Examiner*—Jayme A. Huleatt
*Attorney, Agent, or Firm*—Lorance L. Greenlee

[57] ABSTRACT

A Tn-Mob element is provided comprising a transposon with a Mob-site inserted therein. Vectors and bacterial strains are provided containing the Tn-Mob element, as well as methods for its use. Such methods include the production of plasmid free bacterial strains.

27 Claims, 4 Drawing Figures

Construction of an RP4-Mobilisator-strain

Coselection on KmTc
in recA⁻ backround

Spontaneous integration of
RP4 into the chromosome

Curing of pSR120.

GENE TRANSFER VECTOR

We disclose herein a type of DNA vector useful for genetic engineering manipulations of a wide variety of gram-negative bacteria, and methods for gene transfer between such bacteria, using the type of vector disclosed herein.

The field of genetic engineering of microorganisms, including recombinant DNA technology, developed, in large measure, on the basis of a vast store of detailed, basic knowledge of the genetics of *Escherichia coli* (hereinafter "*E. coli*") and an extensive array of DNA vectors, plasmids, and phages specifically developed with the aid of such knowledge for use in *E. coli*. Although *E. coli* is itself classified as a gram-negative bacterium, most of the DNA vectors and phages developed for use in *E. coli* are unsuitable for use in other gram-negative bacteria, outside a relatively limited group of bacteria closely related to *E. coli*, for example, Salmonella. Nevertheless, there are many gram-negative strains of current commercial utility, the genetic modification of which will provide substantial economic benefit. Examples of such gram-negative strains include members of the following genera: Rhizobium, Agrobacterium, Pseudomonas, Klebsiella and Azotobacter.

There are several barriers that prevent the direct use of *E. coli* vectors and phages in a broad range of gram-negative bacterial strains. One such barrier is the fact that most of the plasmids commonly used as vectors in *E. coli* are unable to replicate normally in most other gram-negative strains. Another barrier is that efficient plasmid transfer by conjugation between *E. coli* and other gram-negative strains, or between other gram-negative strains, does not occur with most widely used *E. coli* vectors. Furthermore, other means for introducing DNA into most gram-negative strains are poorly developed outside of *E. coli* and its close relatives (hereinafter referred to as the *E. coli* group). Transformation of gram-negative strains outside of the *E. coli* group has been demonstrated in some instances; however, the reported efficiencies of transformation have been much lower than those obtainable with *E. coli*. While it is possible that higher frequencies of transformation could be obtained for individual gram negative strains by extensive trial and error modification of transformation conditions, it would be desirable to develop vectors that can be transferred by general means applicable to a wide range of gram-negative bacteria.

The drug-resistance plasmid RP4 is known to be transferable across a broad range of gram-negative host bacteria. See Datta, N., et al., *J. Bact.* 108, 1244 (1971); Datta, N. and Hedges, R. W., *J. Gen. Microbiol.* 70, 453 (1972); Olsen, R. H. and Shipley, P., *J. Bact.* 113, 772 (1973); and Beringer, J. G., *J. Gen. Microbiol.* 84, 188 (1974). Modifications to RP4, to make it useful for genetic manipulation of gram-negative strains, have been reported in the prior art. In particular, RP4 has been modified for use as a vehicle for transposon mutagenesis. Beringer, J. E. et al., *Nature* 276, 633 (1978) reported the transfer of the transposon Tn5 to Rhizobium using pPH1, a broad host range plasmid of the IncP incompatability group containing DNA of bacteriophage Mu and Tn5 inserted into the plasmid. Transfer was effected by conjugation between *E. coli* carrying pPH1 (with inserted Mu and Tn5) and a recipient Rhizobium strain. The effect of the Mu insertion was to render the plasmid unstable in the recipient strain so that the transferred plasmid was ultimately eliminated. The transposon could be rescued in recipient cells in which a translocation had occurred prior to elimination of the plasmid. Plasmids constructed in this manner have been termed "suicide plasmids." The use of such plasmids to introduce random mutations into Rhizobium strains has been reported by Meade, H. M., et al., *J. Bact.* 149, 114 (1982), and in Agrobacterium by VanVliet, F. B., et al., *Plasmid* 1, 446 (1978).

A number of difficulties have been found to be associated with the use of RP4, or other plasmids of incompatibility group P, carrying the Mu genome and Tn5 in transposon mutagenesis. In some instances, the yield of transconjugants was very low, as measured by the acquisition of a drug resistance associated with the transposon. In many cases, the frequency of a transferred drug resistance was not significantly higher than the spontaneous resistance frequency. In other cases, stably replicating derivatives of the "suicide plasmid" arose, presumably by a deletion of the Mu insert. Such mutant plasmids simulate Tn5 transposition events and it is very time consuming to distinguish between Tn5 insertions and other phenomena, such as the acquisition of a stably replicating plasmid. Furthermore, it was frequently the case that mutations occurred, not only by transposon insertion into the recipient genome, but also by transfer of the Mu phage DNA from the plasmid to the recipient genome. Mutations caused by Mu insertion occurred at sites remote from the transposon insertion site and could not be cloned subsequently, since no readily identifiable marker was associated with a Mu insertion.

In order to facilitate discussion of the invention, the following definitions are provided:

Replicon: a fundamental unit of replication comprising all the genetic elements sufficient to confer autonomous replication in a bacterial cell, together with the DNA whose replication is controlled thereby. The bacterial chromosome, plasmids and phage DNA's are examples of replicons existing in a bacterial cell. Individual replicons differ in the extent to which they are functional in different host cell species. Many of the replicons commonly employed as plasmids for genetic engineering are functional only in bacteria of the *E. coli* group, such as members of the genera Escherichia and Salmonella. Such replicons are termed narrow host range replicons. Others, such as RP4, are able to replicate in a wide range of gram-negative bacterial hosts, and are termed herein broad host range replicons.

oriT: Site of origin of transfer replication. The mechanism of DNA transfer by bacterial conjugation includes a replication of the plasmid in which a break is introduced into one strand of duplex plasmid DNA, DNA replication then commences at the site of the break, together with transfer of the cut strand to the recipient cell. Some authors have used the designation nic, to indicate the site of the single-stranded break which initiates transfer replication. The term nic is considered to be equivalent to oriT.

Mob-site: A genetic locus necessary for mobilization of a plasmid transferrable by bacterial conjugation. The Mob-site is believed to include oriT. The Mob-site is considered to be the locus of certain trans-acting functions coded by tra genes. The existence of a Mob-site is a necessary condition for transfer; however, the tra functions must also be provided. Since the latter act in trans, the genes which code for them may be located elsewhere in the cell; for example, on another replicon. Tra functions and Mob-sites also differ with respect to host range. For example, the tra functions and Mob-site of the F factors are limited in function to conjugal transfers between members of the E. coli group. By contrast, the tra functions and Mob-site of the plasmid RP4 permit its conjugal transfer over an exceedingly wide range of gram-negative organisms.

The genetic analysis and isolation of genes has been greatly facilitated in recent years by the use of transposons. Transposons are special DNA segments which have certain structural features and carry within them certain genes which enable them to be transferred as a unit in a random fashion from one genetic locus to another, with a characteristic frequency. Typically, a transposon will contain one or more drug-resistance genes. These provide convenient selection markers to identify the presence of the transposon and to facilitate cloning of any DNA segment containing a transposon. Insertion of a transposon may occur within a gene, resulting in loss of function for that gene. Transposon mutagenesis, combined with restriction site mapping and cloning provides an extremely powerful and rapid technique for genetic and physical analysis of an organism, together with the ability to clone a desired gene of the organism. Until recently, the techniques of transposon mutagenesis and molecular gene cloning have been restricted to E. coli and closely related organisms.

The use of transposons has been hitherto limited to applications exploiting their ability to transfer from one replicon to another with a certain frequency. The transfer is accompanied by insertion of the transposon in the recipient replicon. Insertion occurs either at sites distributed at random or distributed with high frequency throughout the recipient genome. Insertion does not appear to depend on sequence homology at the insertion site. A transposon insertion within a gene results in gene inactivation and consequent loss of the function specified by the inactivated gene. Transposons carrying an antibiotic resistance gene have been widely used, since acquisition of such a transposon can be readily detected by the acquisition of antibiotic resistance. [For general reviews of transposon structure and function, see Starlinger, P., Plasmid 3, 241 (1980); and Calos, H. and Miller, J. H., Cell 20, 579 (1980)].

The use of transposons to introduce extraneous genes is less well developed in the prior art. The formation of cointegrates has been reported to occur, fusing a replicon bearing a transposon with another replicon coexisting in the same cell. The transposon Tn5 has a single BamHI site located in a region that is nonessential for transposon function and outside the gene for kanamycin/neomycin resistance located on the transposon. (Resistance to both antibiotics is conferred by the same gene.) The BamHI site has been used to provide an additional drug-resistance marker for Tn5, by inserting a streptomycin resistance gene at that site, Hirschel, B. J., et al., Proc. Nat. Acad. Sci. U.S.A. 79, 4530 (1982).

The direct use of transposons to transfer genes is limited by the fact that no means presently exists to control the site of transposon integration. Consequently, transposons have not been widely used to transfer genes from one organism to another.

SUMMARY OF THE INVENTION

The present invention provides a modified transposon, a DNA vector comprising the modified transposon, and a method of using the vector and modified transposon to transfer DNA from one bacterial strain to another. The transposon is modified to include a Mob-site inserted at a site so located that the insertion does not interfere with functions of transposibility or with any selection markers. The vector is designed to be transferrable to a broad range of gram-negative recipient bacteria. By including a Mob-site within the transposon inserted in the vector, the vector is provided with the ability to be transferred by conjugation from a donor host cell carrying the vector to a recipient cell. The vector is further provided with narrow host range replication functions such that vector replication can only occur in a limited range of host strains. Preferably the vector is unable to replicate in intended recipient cells. The persistence of transposon-borne drug resistance (or other detectable phenotypic trait) is therefore an indication that the transposon has been transferred to a replicon within the recipient cell, either its main chromosome or a plasmid. The vector is termed herein a Tn-Mob vector, to indicate that it carries a transposon having a Mob-site within the transposon. More specifically, a given Tn-Mob vector is identified by the name of the modified transposon used in its construction. For example, where Tn5 is modified by insertion of a Mob-site and inserted within a vector, the resulting vector is designated a Tn5-Mob vector. The modified transposon itself is designated a Tn-Mob element.

Conjugational transfer of a Tn-Mob vector requires the presence of transfer (tra) functions capable of acting on the Mob-site. The tra functions may be provided by a plasmid or by a specifically constructed strain having the tra functions integrated into chromosomal DNA. Examples of such strains are provided herein.

The construction and use of the modified transposon and Tn-Mob vector of the present invention are disclosed herein by reference to the use of a Mob-site and tra functions derived from plasmid RP4, and by narrow host range vectors limited to replication within the E. coli group. Such transposons and vectors exploit the great variety of vectors developed for use in E. coli, and the broad range of gram-negative bacterial strains in which the Mob-site and tra functions of RP4 are functional. Other kinds of narrow host range replicons and other Mob-site and tra functions may be used, as desired, by those of ordinary skill in the art, following the principles and teachings disclosed herein.

DETAILED DESCRIPTION OF THE INVENTION

The invention is described in detail by reference to a specific embodiment derived from modification of transposon Tn5, designated a Tn5-Mob vector. However, the principles of the invention may be more broadly applied to the construction of vectors comprising other modified transposons, the choice of which depends upon the desired properties of a given transposon, including selection markers, which are matters of choice available to those of ordinary skill in the art. Tn5 was employed in the embodiments exemplified herein, since it is known to contain a single BamHI site at a convenient locus for the insertion of an extraneous DNA fragment, such as a fragment comprising a Mob-site. Any other transposon can be used, provided there exists within its borders an insertion site (typically a restriction site) where the insertion of additional DNA does not interfere with normal transposon function or any selection marker carried on the transposon. A determination that such an insertion site exists is a matter of routine for those of ordinary skill, and can be carried out without undue experimentation. Furthermore, the choice of mobilization system is one which may be made by those of ordinary skill based upon considerations of host range and operating convenience. In the exemplified embodiments, the mobilization system of the mobilizable broad host range plasmid RP4 was employed. A DNA segment of RP4 comprising the Mob-site but excluding the tra functions was isolated and inserted in the BamHI site of Tn5.

It is considered preferable to employ, as carrier of the transposon-Mob segment, a narrow host range replicon that does not replicate in the intended recipient host strain. In that way, selection for persistence of the transposon in the recipient insures the recovery of colonies in which the transposon has transferred to a stable replicon of the recipient, either the recipient chromosome or a stably replicating plasmid. It is most preferred to employ the narrow host range replicons of $E.$ $coli$ vectors that have been designed for genetic engineering work in $E.$ $coli.$ Such replicons, e.g., pBR325, pACYC177, pACYC184 and the like, are generally well characterized, have conveniently located restriction sites, and have a narrow host range for replication, generally limited to the $E.$ $coli$ group. Transposon-Mob vectors derived from narrow host range replicons replicating in the $E.$ $coli$ group are advantageous for use with gram-negative recipients including, but not limited to, bacteria of the genus Rhizobium, Agrobacterium, Pseudomonas, Klebsiella, Azotobacter, and Rhodopseudomonas.

In general use, a Tn-Mob element can be inserted into any replicon, either chromosomal, plasmid or phage, of any gram-negative bacterium which does not allow the replication of the Tn-Mob vector. The target replicon, i.e., the replicon to which the Tn-Mob is transferred in the recipient strain, is rendered mobilizable. By providing the tra functions in the recipient cell, (for example, by transferring RP4 to the recipient strain), the target replicon is mobilized and transferred, by conjugation. A bacterial strain serving as the recipient in such a conjugal transfer is termed herein the target replicon recipient, since it is the recipient of the transfer of the target replicon mobilized by insertion of the Tn-Mob element. Where the target replicon is the chromosome of a given strain, insertion of the Tn-Mob element allows mobilization of chromosomal genes with a frequency comparable to the transfer of chromosomal genes from an $E.$ $coli$ Hfr strain. Using the Tn-Mob system, chromosomal genes of gram-negative strains can be mapped very easily. For many gram-negative strains of commercial interest, chromosome mapping experiments are needed in order to make genetic manipulations of these strains. The transfer of chromosomal genes by Tn-Mob mobilization is also useful for introducing chromosomal genes of interest into appropriate recipients, thereby providing commercially useful recombinants, either by homologous recombination or by other means known in the art.

The great majority of naturally occurring plasmids are nontransmissible. However, insertion of a transposon-Mob element can render such plasmids transmissible in the presence of the tra functions of RP4. Therefore, the transposon-Mob vector of the present invention is useful to provide high frequency transfer of any plasmid of interest into any recipient of interest in order to combine the genetic capabilities of the transferred plasmid with those of the recipient strain of interest. A distinct advantage to plasmid transmission by conjugation as provided by the present invention is that there is no upper limit to the size of the DNA molecules which can be transferred from one strain to another. In contrast, prior art techniques involving in vitro isolation of plasmid DNA followed by transformation are limited to the transfer of plasmids sufficiently small that the DNA can be isolated intact. DNA molecules larger than about $10^8$ d are difficult to isolate intact because such molecules are susceptible to breakage by mechanical shear stresses induced by in vitro operations of stirring, pouring and the like. Transposon-Mob vectors make it possible to create a great variety of new strains, for example, by introducing plasmids which carry symbiotic genes to extend the symbiotic host range, to introduce genes of specialized biochemical pathways, to combine the capabilities for special biosynthetic or biodegradation capabilities within a single strain, and to introduce genes for resistance against detrimental environmental influences, such as extremes of temperature, pH or ionic strength that may be encountered in certain industrial or waste water management processes.

Additionally, a transposon-Mob vector is useful for mobilizing cryptic plasmids, transferring such plasmids to recipients having a well-defined genetic background in order to determine the functions of such cryptic plasmids. Furthermore, it is possible to select the donor strain after transfer of the plasmid so that strains which have been cured of a given plasmid can be isolated once the plasmid is mobilized and transferred. We present herein an example showing the mobilization of the sym megaplasmid of $R.$ $meliloti$ and its transfer to $Agrobacterium$ $tumefaciens.$ The Tn-Mob vector is also useful in the construction of plasmid-free strains of gram-negative bacteria. Such strains are in turn useful for reconstructing genetically engineered strains with defined properties. Bacteria of the genera Agrobacteria and Rhizobia, for example, typically contain large plasmids carrying genetic information unrelated to the commercially significant functions of tumor induction and nitrogen fixation, respectively. Once the endogenous plasmids are removed, strains having more defined and limited functions can be constructed, by introducing one or more plasmids conferring known, desired characteristics. In this way, interference by unknown genetic factors and competition for energy resources by extraneous genetic information are reduced or eliminated. A plasmid-free strain of $A.$ $tumefaciens$ has been constructed using a Tn-Mob vector of the invention.

In general, a Tn-Mob vector is first used to transfer the Tn-Mob element, together with any selectable marker, to a heat-curable plasmid that can replicate in the host cell harboring the resident plasmid to be removed, but which is incompatible with the resident plasmid. The heat-curable plasmid bearing Tn-Mob and selectable marker is then introduced into the host cell by conjugation. By growth of host transconjugants under conditions that select for the presence of the marker, those transconjugants which have lost the resident plasmid due to incompatibility (or any other mechanism) and retained the plasmid bearing Tn-Mob and selectable marker are selected. A plasmid-free strain can then be generated by a convection heat-curing procedure followed by selection for loss of the selectable marker associated with the plasmid.

The construction of a specific transposon-Mob vector, its selection and use in specific instances are described in detail in the following examples. The abbreviations used in the examples and elsewhere in the specification are those commonly accepted for publication in standard journals such as those cited herein. When not otherwise specified, reagents and materials described herein are obtainable from commercial sources. Unless otherwise specified, restriction enzymes, DNA ligase and other enzymes were used under conditions specified by the manufacturer or as set forth in the referenced published procedures. Where not otherwise specified, standard procedures, such as those set forth in *Methods in Enzymology* Vol. 68, R. Wu, Ed. (Academic Press, New York 1979) were employed.

EXAMPLE 1

Construction of a Mobilizing Strain

Two derivatives of plasmid RP4 were forced by the choice of selection conditions to coexist in a recA$^-$ *E. coli* host. RP4-2-Tc::Mu was derived from RP4-2 by insertion of phage Mu into the tetracycline resistance gene of RP4-2. (See U. B. Priefer et al. in *Antibiotic Resistance, Transposition and Other Mechanisms*, (S. Mitshuhashi, L. Rosival and V. Krcmery, eds.) Springer Verlag, Berlin (1980), page 91 and R. Simon, ibid., page 35, for description of RP4-2 and the general methodology of Mu insertion.) Plasmid RP4-2-Tc::Mu is ampicillin-sensitive (Ap$^s$), tetracycline-sensitive (Tc$^s$), kanamycin-resistant (Km$^r$) and tra+. The plasmid was introduced into a recA$^-$ strain of *E. coli* by conventional conjugation. The recA$^-$ strains used in this study were CSH52, (Miller, J. H., *Experiments in Molecular Genetics,* Cold Spring Harbor Laboratory (1972); C600(recA), (Appleyard, R. K., Genetics 39, 440 (1954); parent strain: ATCC #23724; and *E. coli*294-(recA), Cold Spring Harbor Laboratory, New York; parent strain: ATCC #31446. Both C600 and 294 were made recA$^-$ by cotransduction of a known recA$^-$ deletion mutant with a closely linked selectable marker identified by Tn10 insertions, using phage P1 as the transducing agent. Approximately 50% of Tc$^r$ transductants were recA$^-$.

The second RP4 derivative employed was pSR120, a fusion product of plasmids pSR100 and ColE1. pSR100 is a "mini RP4", described by Simon et al., supra, isolated as a deletion of RP4 lacking kanamycin resistance and tra functions. pSR120 was derived from pSR100 and ColE1 by joining the two at their unique EcoR1 sites, after digestion with EcoR1 endonuclease and rejoining with DNA ligase. pSR120 was Ap$^r$ and Tc$^r$.

The plasmid pSR120 was introduced into a recA$^-$ strain of *E. coli* containing the plasmid RP4-2-Tc::Mu by transduction with phage P1. The cells were plated on medium containing 25 mg/l kanamycin and 5 mg/l tetracycline. The intial selection yielded several hundred colonies which were very small, indicating poor growth. However, after prolonged incubation, up to three days, a few normal-sized colonies were observed. Cultures derived from these normally-growing colonies were further characterized by gel electrophoretic analysis of plasmid DNA and ability to transfer chromosomal genes. In this manner it was possible to identify strains which retain the Km$^r$ and Tra+ phenotype but which lacked RP4-2-Tc::Mu, indicating that the latter plasmid was integrated in the chromosome.

The plasmid pSR120 was cured from strains containing RP4-2-Tc::Mu integrated in the chromosome. The strain to be cured was grown for about 40 generations in LB medium (Luria broth) (Miller, J., *Experiments in Microbial Genetics,* Cold Spring Harbor Laboratory, New York), containing 100 mg/l acridine orange (AO). After the AO treatment, the culture was enriched for Tc$^s$ cells by incubation in the presence of 5 mg/l tetracycline and 100 mg/l cycloserine. Growth in the presence of tetracycline was lethal to Tc$^r$ cells in the presence of cycloserine. The cycloserine enrichment procedure was repeated twice. Gel electrophoretic analysis of plasmid DNA isolated from Tc$^s$ clones showed that pSR120 was lost. Three clones have been isolated and characterized as described, and their characteristics are shown in the following table:

| strain number | integrated plasmid | resistance markers RP4 | chrom. | other important properties |
|---|---|---|---|---|
| S 68-7 | RP4-2(Tc::Mu) | Km | Sm | Thi, Pro, His, su$^-$ |
| SM 10 | " | Km | — | Thi, Thr, Leu, su$_{III}$ |
| S 17-1 | RP4-2(Tc::Mu) (Km::Tn$^7$) | Tp-Sm | — | Pro, res$^-$mod$^+$ |

Figure 1:
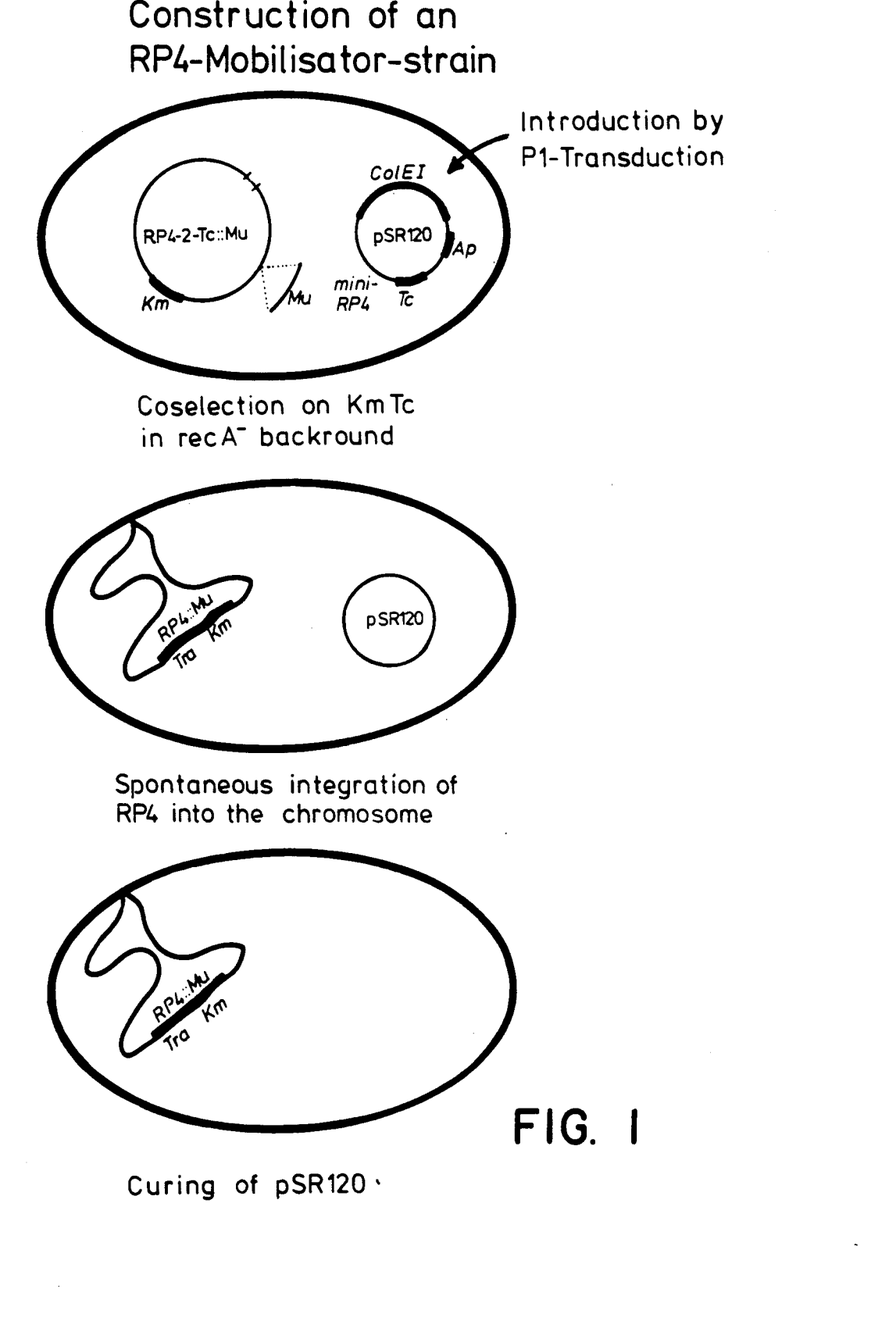

Strain S68-7 was obtained using *E. coli* CSH52 as the recA$^-$ host, strain SM10 was obtained using *E. coli* C600 and S17-1 was obtained from *E. coli* 294. In addition, in strain S17-1, the Km$^r$ was abolished by a Tn7 insertion. Strain S17-1 carries resistance to trimethoprim (Tp) and Streptomycin (Sm), and is restriction-deficient. A schematic representation of the construction of a mobilizing strain as described herein, is shown in FIG. 1.

EXAMPLE 2

Construction of Mobilizable Vector Plasmids

The following constructions were based on the strategy of inserting random fragments of RP4, generated by partial Sau3A digestion, into the BamHI site of an *E. coli* vector, e.g., pACYC184 and pBR325. The hybrid plasmids containing the RP4-specific Mob-site were identified by mating experiments using a mobilizing strain, constructed as described in Example 1, as donor.

Partial digestions of RP4 DNA with Sau3A were carried out under reaction conditions empirically chosen to provide an optimum size range of RP4 fragments. The conditions of buffer, reaction time and temperature were as described by the manufacturer of the restriction enzyme. However, the amount of enzyme employed was reduced by making a series of dilutions of the restriction enzyme. The resulting mixtures of fragments were subjected to agarose gel electrophoresis to determine the distribution of fragment sizes. Digest yielding RP4 DNA fragments mostly smaller than about 3 kb were used for the subsequent ligation reaction. Some variation was observed between batches of enzyme. In one experiment, a 1:125 dilution of Sau3A endonuclease yielded a fragment distribution in which the majority of fragments appeared to be greater than 2 kb and a substantial portion were greater than 3 kb, while a 1:100 dilution of the enzyme yielded fragments, the majority of which were smaller than 3 kb.

The vector plasmid, either pACYC184 or pBR325 was linearized by digestion with BamHI endonuclease, using standard reaction conditions for complete digestion. Since these vector plasmids possess a unique BamHI site, the resulting digestion yielded linear molecules of uniform size.

In the ligation reaction, 20 μl of partial Sau3A-digested RP4 DNA prepared as described, supra, (about 20 μg/ml) and 10 μl BamHI digested pACYC184 (or pBR325) DNA, about 20 μg/ml, were mixed with 3 μl ATP (1 mg/ml) and 1 μl DNA ligase in a standard DNA ligase reaction buffer (*Methods in Enzymology*, Vol. 68, supra.) incubated at room temperature for 3 hours. The resulting hybrid plasmids were used to transform the mobilizing strain S68-7 (Example 1) by a standard transformation procedure (Miller, J. supra). Transformants were selected by growth on agar plates containing PA-medium [17.5 g/l Penassay broth (Difco Laboratories, Detroit, Mich.] supplemented with 100 mg/l chloramphenicol. Several hundred colonies were picked and grown in mixed liquid culture to mid-log phase, constituting a donor culture for subsequent mating.

The recipient strain was a Nalidixic acid-resistant ($Nx^r$) strain of *E. coli* C600. Approximately $5 \times 10^8$ donor cells were mixed with $10^9$ recipient cells, collected on a nitrocellulose filter and incubated on pre-warmed PA medium for 2 hours at 37° C. The cells were then re-suspended in liquid medium and aliquots were spread on agar selection plates containing PA medium supplemented with chloramphenicol (100 mg/l) and nalidixic acid (100 mg/l). The plasmid construction and selection system is shown schematically in FIG. 2. Selection for combined chloramphenicol and nalidixic acid resistance yields cells in which the recombinant plasmid containing the $Cm^r$ gene has been transferred to the $Nx^r$ recipient. In principle, only mobilizable recombinant plasmids could be transferred.

From the resulting colonies, a selected clone was characterized and found to obtain a mobilizable derivative of pACYC184. The plasmid was mobilized by the RP4 transfer functions with a frequency of 100% in *E. coli* matings. As shown by restriction analysis, the plasmid contained a DNA insert of 2.6 kb. The resulting plasmid was designated pSUP101.

Using the same procedure, the Mob-site of RP4 was cloned into the vector plasmid pBR325. The resulting mobilizable derivative, designated pSUP201, was found to contain an insert of only 1.9 kb, yet was efficiently mobilized as pSUP101. Therefore, the Mob-site was contained within a DNA fragment not larger than 1.9 kb.

Figure 2:
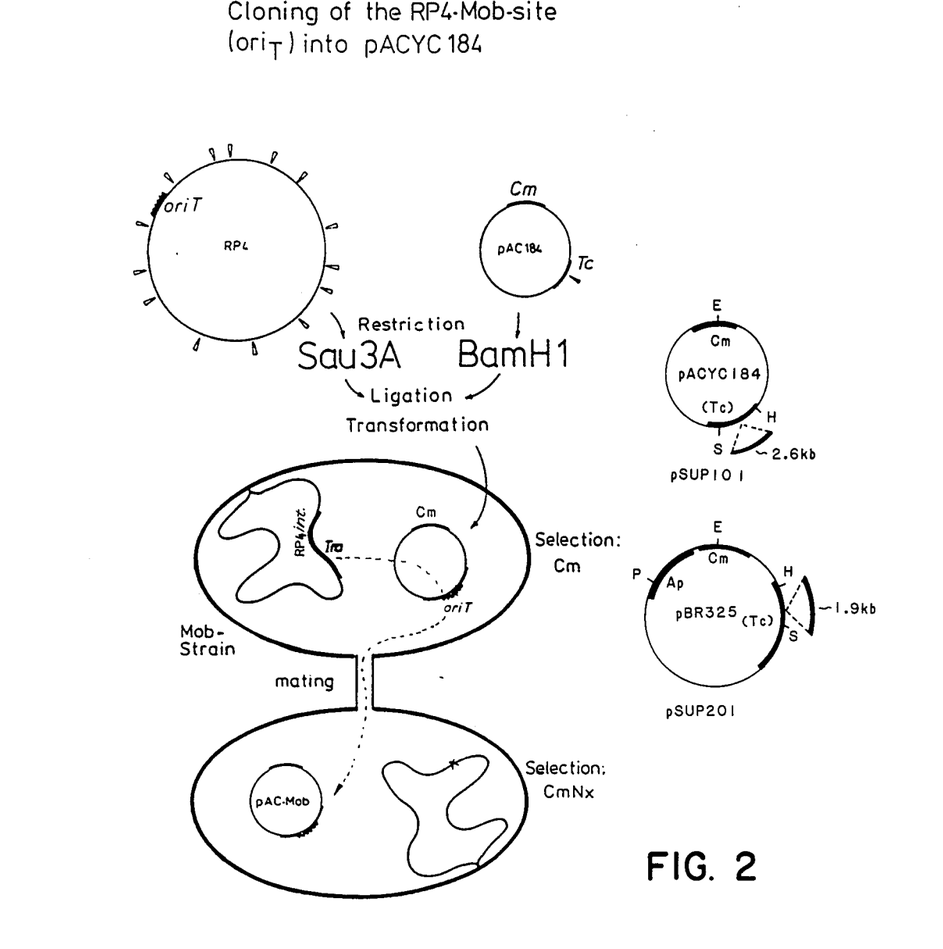

Partial restriction and genetic maps of pSUP101 and pSUP201 are shown in FIG. 2.

EXAMPLE 3

Construction of a Tn5-Mob Vector

The plasmid pBR325 was digested with BamHI endonuclease. Since the plasmid has a single BamHI site, the digestion converts the plasmid to linear form. The linear plasmid DNA (approximately 10 μg) was then digested with 5 μl of Sau3A endonuclease diluted 1:10 by volume for 15 minutes at 37° C. under standard reaction conditions for Sau3A endonuclease. The purpose of the partial digestion was to remove a small fragment adjacent to the BamHI site at one of the ends of the linear molecule to produce a small deletion in the tetracycline resistance gene.

The DNA fragments produced by the partial Sau3A digestion were incubated with DNA ligase, under standard ligation reaction conditions. After completion of the reaction, aliquots of the reaction mixture were used to transform *E. coli* HB101. Transformants were selected for ability to grow on plates containing Cm and subsequently screened for resistance to ampicillin and sensitivity to tetracycline ($Ap^r$, $Tc^s$). Further characterization of a $Tc^s$ derivative by restriction endonuclease digestion and gel electrophoresis of the resulting fragments demonstrated that it had a deletion of at least a part of the $Tc^r$ gene including the BamHI site. The resulting plasmid is designated herein pBR325(Bam−).

Figure 3:
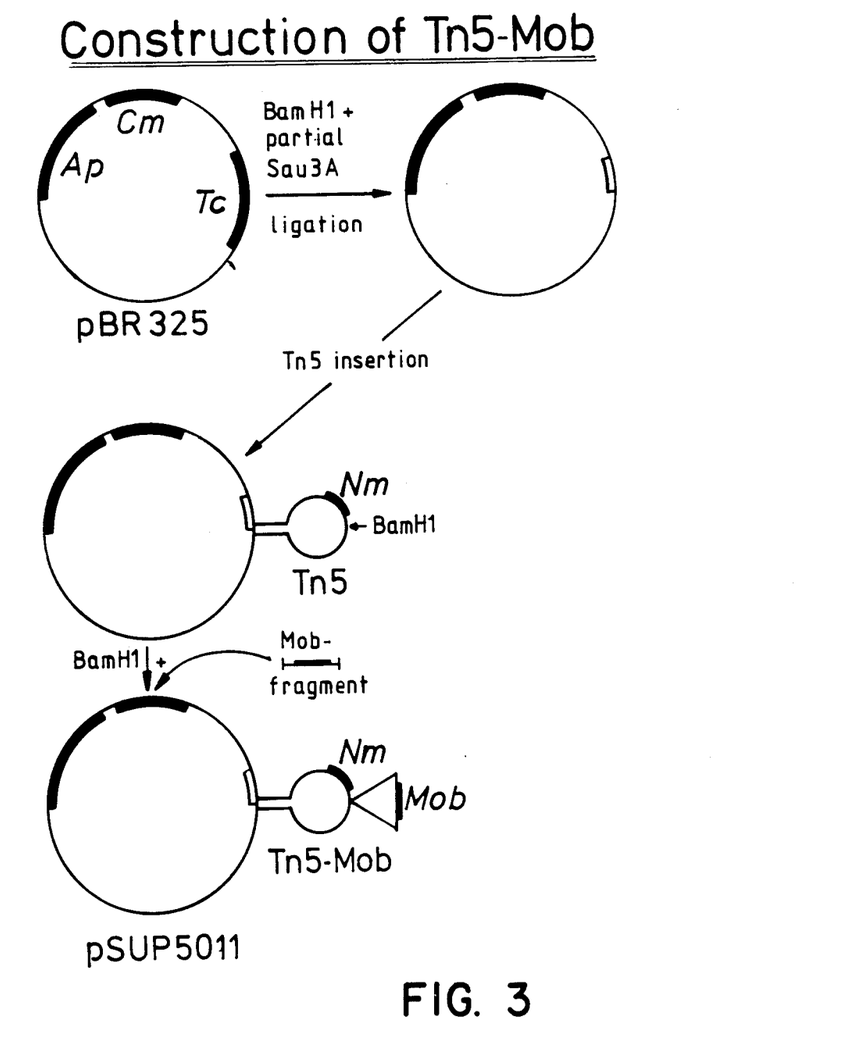

The plasmid pBR325(Bam−) was transformed into an *E. coli* strain carrying the transposon Tn5 (*E. coli* S605, which is essentially *E. coli* C600 having Tn5 inserted in a gene of the methionine biosynthesis pathway). In this strain Tn5 can transpose spontaneously onto the plasmid. A selection strategy was devised based upon transposition of Tn5 from a chromosomal locus to a plasmid locus. The presence of Tn5 on a multi-copy plasmid ought to result in a resistance to higher kanamycin levels than the presence of a single copy integrated in the chromosome. To select for this eventuality, 0.3 ml of a saturated overnight culture of S605 (pBR325(Bam−) was spread on an agar plate containing Penassay broth (Difco Laboratories, Detroit, Mich.) containing Cm (50 mg/l) and Nm. The Nm was introduced onto the plate as a 0.2 ml droplet of concentrated Nm solution (100 mg/ml) on the center of the plate. The Nm solution was allowed to diffuse overnight prior to seeding the plate. As a result of diffusion, a concentration gradient of Nm was present on the plate. Colonies containing Tn5 on a multicopy plasmid should grow preferentially near the center of the plate. A number of colonies picked near the center of the plate were found to contain pBR325 with an inserted Tn5. The plasmid of one such colony was isolated and found to carry Tn5 at the former position of the Tc gene in the vector, as shown in FIG. 3.

The resulting pBR325::Tn5 vector molecule was treated with BamHI endonuclease to generate linear vector molecules, and a DNA fragment containing the Mob-site was inserted at the BamHI site. A DNA fragment containing the Mob-site was obtained by partial digestion of pSUP101 DNA, described supra in Example 2, using partial Sau3A digestion conditions as described therein. The Mob fragment DNA was ligated to BamHI-digested pBR325::Tn5, under standard DNA ligase reaction conditions. The resulting plasmids were transformed into strain S17-1 selected for kanamycin resistance, in order to test for mobilizability of kanamycin resistance using a kanamycin-sensitive recipient. A clone having the properties of carrying mobilizable kanamycin resistance was isolated and the plasmid was designated pSUP5011, a partial genetic and restriction map being shown in FIG. 3. In addition to kanamycin resistance and mobilizability, the transposon of pSUP5011 expresses its transposon functions, so that pSUP5011 can also be used for random Tn5 mutagenesis in Rhizobia or other gram-negative bacteria.

EXAMPLE 4

Mobilization of the *R. meliloti* megaplasmid

The mobilization was carried out in two stages. Stage 1 was the transfer of pSUP5011 into *R. meliloti* and selection of *R. meliloti* recipients carrying the transposon. Stage 2 included mobilization of the *R. meliloti* replicon containing inserted Tn5 Mob, conjugal transfer thereof to *Agrobacterium tumefaciens* and selection and characterization of an *A. tumefaciens* recipient carrying the *R. meliloti* megaplasmid.

Figure 4:
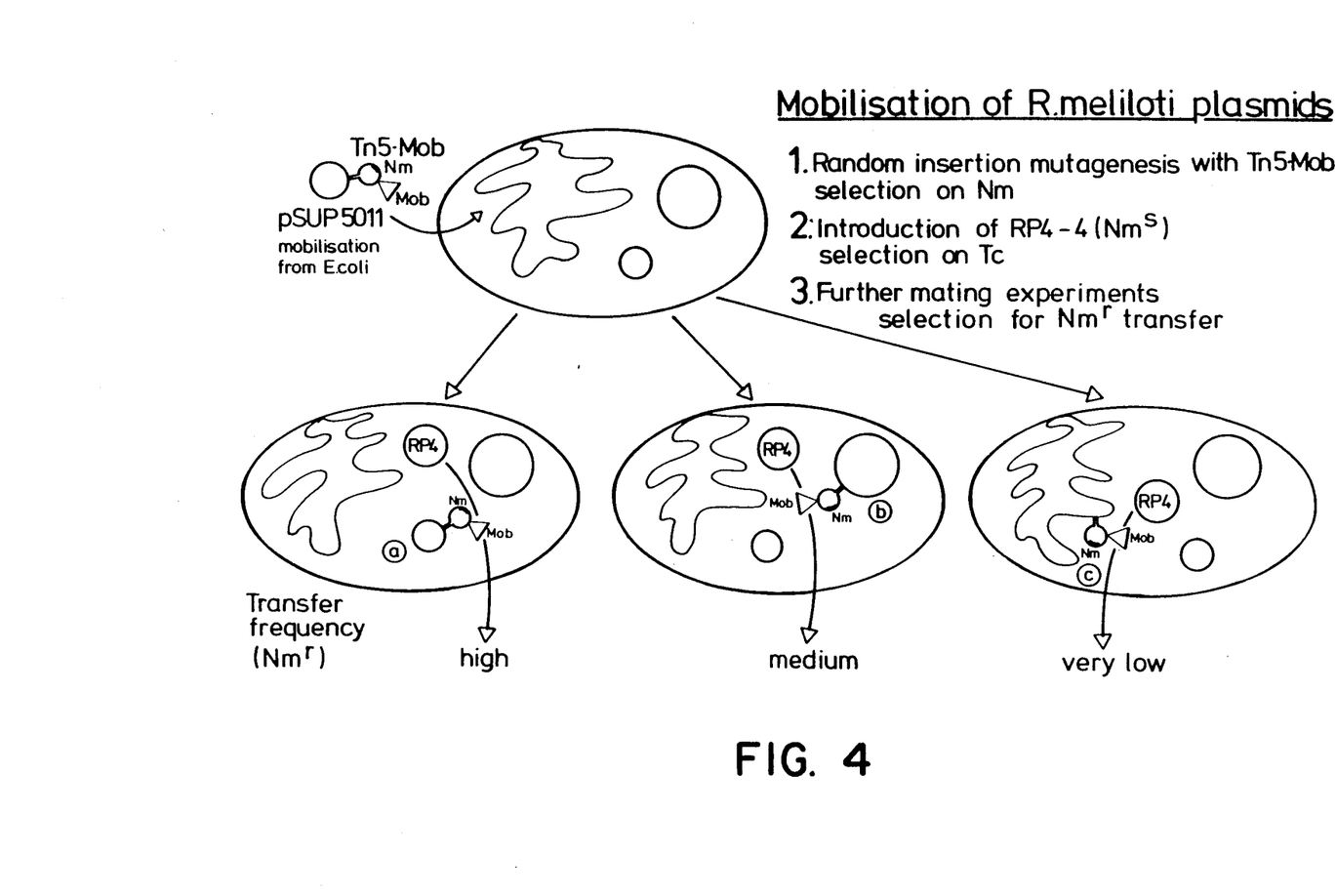

*E. coli* SM10 carrying pSUP5011 (Example 3) was transferred to *R. meliloti* 2011 ($Sm^r$) by mating on nitrocellulose filters. Cultures of donor and recipient cells were mixed in liquid medium, collected on nitrocellulose filters and incubated for several hours at 30° C. The conjugation mix was subsequently resuspended in buffer and plated onto selected medium containing Sm (600 mg/l) and Nm (100 mg/l). The presence of streptomycin kills donor cells and the presence of neomycin selects against those recipients which did not receive the transposon transferred to a stable replicon. The frequency of $Nm^r$ transconjugants was about $10^{-5}$ per recipient. A total of 30 $Nm^r$ R. meliloti clones were picked, grown in non-selective medium and mobilized by introduction of an RP4 derivative. The mobilizing helper plasmid RP4-4 (a Nm-sensitive derivative of RP4), was introduced by conventional conjugation (see step 2 in FIG. 4). The donor was E. coli C600(RP4-4), the recipients were the 30 Tn5-Mob containing R. meliloti clones just described. Selection was on medium containing Sm (600 mg/l) (against the donor cells) and Tc (5 mg/l) (for the introduction of RP4-4).

The target replicon recipient was a rifampicin resistant ($Rif^r$) strain of A. tumefaciens, either LBA290 or LBA275. The matings were performed as described supra on nitrocellulose filters to optimize the transfer conditions. Transconjugants were selected on medium containing Nm and Rif. Twelve of the thirty donor clones transferred neomycin resistance with a frequency of about $10^{-6}$ per recipient, the expected frequency for transfer of a plasmid. The resulting strains were characterized by analysis of the plasmid DNA on electrophoresis. The strains were lysed essentially as described by Eckhardt, T., Plasmid 1, 584 (1978). The DNA was fractionated by electrophoresis in 0.8% (w/v) agarose gel in Tris-borate buffer for 3 hours at 120 V and stained with ethidium bromide. The DNA bands were visualized under ultraviolet light. A band corresponding to the R. meliloti megaplasmid was readily detected in the target replicon recipient A. tumefaciens strains previously identified as megaplasmid recipients. The megaplasmid was stably maintained in the A. tumefaciens transconjugant clones. These clones were tested for the ability to nodulate alfalfa plants. The A. tumefaciens clones that contained the R. meliloti megaplasmid were found to be capable of nodulating alfalfa. The mobilization and transfer steps are shown diagrammatically in FIG. 4.

EXAMPLE 5

Construction of a Plasmid-Free Strain of *Agrobacterium tumefaciens*

Using pSUP5011 (Example 3) as donor, Tn5-Mob was inserted into the smallest of the plasmids harbored by R. meliloti 41, designated pRm41a, essentially as described in Example 4. Insertion into pRm41a was identified by agarose gel electrophoresis of DNA transferred to a plasmid-free recipient from donor strains of cloned R. meliloti $Nm^r$ transconjugants described in Example 4. Transfer of pRm41a-Tn5-Mob was accomplished by mobilizing the plasmid with RP4-4, introduced by conjugation as described in Example 4.

Once a R. meliloti clone carrying pRm41a-Tn5-Mob was identified, it was used as a donor for transfer of the plasmid to A. tumefaciens LBA290, a Ti-plasmid free, $Sm^r$, $Rif^r$ derivative of A. tumefaciens again using RP4-4 to mobilize the plasmid. The mating mixture was selected on plates containing Sm and Nm, where the parental strains were unable to grow and only transconjugants bearing pRm41a::Tn5-Mob could grow. The DNA of transconjugants was fractionated by agarose gel electrophoresis.

Unexpectedly, it was found that recipients of pRm41a::Tn5-Mob had lost the cryptic A. tumefaciens plasmid pC58, although they contained pRm41a::Tn5. It was further discovered that the latter plasmid could be heat-cured.

A transconjugant clone containing only pRm41a::Tn5-Mob was grown at elevated temperature. Surviving clones were screened for Nm-sensitivity. $Nm^s$ clones were further analyzed by agarose-gel electrophoresis. The analysis demonstrated that the clone had lost pRm41a::Tn5-Mob and did not contain any other plasmids. One such plasmid-free A. tumefaciens strain was designated APF-1.

The following strains were placed on deposit with the U.S. Department of Agriculture, Northern Regional Laboratory, 1815 North University Street, Peoria, Ill. 61604:

| Strain | Deposit Date | NRRL Accession # |
| --- | --- | --- |
| E.coli CSH52/pSUP5011 | July 1, 1983 | B-15495 |
| E.coli SM10 | July 1, 1983 | B-15481 |
| E.coli S68-7 | July 1, 1983 | B-15482 |
| E.coli S17-1 | July 1, 1983 | B-15483 |
| A.tumefaciens APF-1 | August 29, 1983 | B-15572 |

We claim:

1. A Tn-Mob vector comprising:
   (a) A replicon functional in E. coli; and
   (b) A Tn-Mob element comprising a transposon containing (i) a functional selection marker, and (ii) a Mob-site and oriT located in a region of said transposon that is not essential to transposability.

2. The Tn-Mob vector of claim 1 wherein the replicon is pBR325, pACYC177 or pACYC184.

3. The Tn-Mob vector of claim 1 wherein the transposon is Tn5.

4. The Tn-Mob vector of claim 1 wherein the Mob-site is derived from RP4.

5. The Tn-Mob vector of claim 1 wherein the transposon is Tn5 modified by having inserted at its BamHI site a DNA segment comprising a Mob-site derived from RP4.

6. The Tn-Mob vector of claim 5 wherein the replicon is pBR325, pACYC184, or pACYC177.

7. The Tn-Mob vector of claim 5 wherein the vector is pSUP5011.

8. A bacterial strain containing and replicating the Tn-Mob vector of claim 1.

9. The bacterial strain of claim 8 wherein the replicon of the Tn-Mob vector is pBR325, pACYC177, or pACYC184.

10. The bacterial strain of claim 8 wherein the transposon of the Tn-Mob vector is Tn5.

11. The bacterial strain of claim 8 wherein the Mob-site of the Tn-Mob vector is derived from RP4.

12. The bacterial strain of claim 8 wherein the transposon of the Tn-Mob vector is Tn5 modified by having inserted at its BamHI site a DNA segment comprising a Mob-site derived from RP4.

13. The bacterial strain of claim 12 wherein the replicon of the Tn5 Mob vector is pBR325, pACYC184, or pACYC177.

14. The bacterial strain of claim 12 wherein the Tn-Mob vector is pSUP5011.

15. A method for mobilizing a target replicon comprising the steps of:

(a) transforming a bacterial cell containing said target replicon with the Tn-Mob vector of claim 1; and
(b) selecting transformants for persistence of the transposon carried on said Tn-Mob vector whereby the selected transformants contain a target replicon mobilized by transfer of said Tn-Mob element thereto, said target replicon being transferrable by conjugation to a target replicon recipient cell in the presence of tra functions capable of acting on said Mob-site.

16. The method of claim 15 wherein the transposon of the Tn-Mob vector is Tn5 modified by having inserted at its BamHI site a DNA segment comprising a Mob-site derived from RP4, and the target replicon is contained in a gram-negative bacterial cell.

17. The method of claim 15 wherein the target replicon is contained in a bacterial cell of the genus Rhizobium.

18. The method of claim 15 wherein the target replicon is contained in a bacterial cell of the genus Agrobacterium.

19. The method of claim 15 wherein said Tn-Mob vector is pSUP5011.

20. A Tn-Mob element comprising a transposon modified by insertion of a Mob-site and oriT into a region of said transposon that is not essential to transposability, said modified transposon also comprising a functional selection marker.

21. The Tn-Mob element of claim 20 wherein the said functional selection marker is drug resistance.

22. The Tn-Mob element of claim 21 wherein said transposon is Tn5.

23. The Tn-Mob element of claim 22 wherein said Mob-site is derived from plasmid RP4.

24. A method for removing a resident plasmid from a host bacterial cell comprising:
(a) transferring the Tn-Mob element of claim 20 to a heat-curable plasmid capable of replication in said host bacterial cell but incompatible with a resident plasmid in said host bacterial cell, thereby providing a mobilizable, incompatible and selectable plasmid;
(b) transferring said mobilizable, incompatible and selectable plasmid to said host bacterial cell by conjugation; and
(c) growing transconjugants of said host bacterial cell under conditions that select for the presence of said mobilizable, incompatible and selectable plasmid, thereby identifying those host bacterial cells wherein said resident plasmid has been removed.

25. The method of claim 24 wherein the host bacterial cell is a strain of the genus Agrobacterium.

26. The method of claim 24 wherein the host bacterial cell is a strain of the genus Rhizobium.

27. A biologically pure culture consisting of the bacterial strain *Agrobacterium tumefaciens* APF-1.

* * * * *